United States Patent [19]
Wang et al.

[11] Patent Number: 5,795,318
[45] Date of Patent: Aug. 18, 1998

[54] METHOD FOR DELIVERING DRUGS TO A VASCULAR SITE

[75] Inventors: Lixiao Wang; Roger Hastings, both of Maple Grove; Paul Buscemi, Long Lake; Sew-Wah Tay, Plymouth, all of Minn.

[73] Assignee: Scimed Life Systems, Inc., Maple Grove, Minn.

[21] Appl. No.: 802,521

[22] Filed: Feb. 20, 1997

Related U.S. Application Data

[60] Continuation of Ser. No. 471,635, Jun. 6, 1995, abandoned, which is a division of Ser. No. 129,860, Sep. 30, 1993, abandoned, which is a continuation-in-part of Ser. No. 55,635, Apr. 30, 1993, abandoned.

[51] Int. Cl.$^6$ .................................. A61F 2/06; A61M 5/00
[52] U.S. Cl. ........................................ 604/8; 623/1
[58] Field of Search ........................... 604/8; 623/1, 11, 623/12

[56] References Cited

U.S. PATENT DOCUMENTS

| | | |
|---|---|---|
| 4,212,304 | 7/1980 | Finney . |
| 4,307,723 | 12/1981 | Finney . |
| 4,464,176 | 8/1984 | Wijayarathna . |
| 4,586,923 | 5/1986 | Gould et al. . |
| 4,643,716 | 2/1987 | Drach .................................. 604/8 |
| 4,681,564 | 7/1987 | Landreneau . |
| 4,694,838 | 9/1987 | Wijayarathna et al. . |
| 4,762,130 | 8/1988 | Fogarty et al. . |
| 4,776,844 | 10/1988 | Ueda . |
| 4,856,516 | 8/1989 | Hillstead . |
| 4,884,557 | 12/1989 | Takehana et al. . |
| 4,913,683 | 4/1990 | Gregory . |
| 4,919,133 | 4/1990 | Chiang . |
| 4,950,258 | 8/1990 | Kawai et al. . |
| 4,968,306 | 11/1990 | Huss et al. . |
| 4,969,890 | 11/1990 | Sugita et al. . |
| 5,021,044 | 6/1991 | Sharkawy . |
| 5,037,404 | 8/1991 | Gold et al. . |
| 5,040,543 | 8/1991 | Badera et al. . |
| 5,052,998 | 10/1991 | Zimmon .................................. 604/8 |
| 5,078,736 | 1/1992 | Behl . |
| 5,087,244 | 2/1992 | Wolinsky et al. . |
| 5,100,429 | 3/1992 | Sinofsky et al. . |
| 5,108,407 | 4/1992 | Geremia et al. . |
| 5,163,928 | 11/1992 | Hobbs et al. . |
| 5,181,911 | 1/1993 | Shturman . |
| 5,211,636 | 5/1993 | Mische . |

(List continued on next page.)

FOREIGN PATENT DOCUMENTS

| | | |
|---|---|---|
| 0 526 102 A1 | 2/1993 | European Pat. Off. . |
| 0 535 874 A1 | 4/1993 | European Pat. Off. . |

OTHER PUBLICATIONS

Drug Delivery Meeting "A Field in take–off", 3–4 Mar. 95, Amsterdam Schiphol Airport Hilton, From The Thoraxcenter Department of Cardiology, Erasmus University Hospital Rotterdam, The Netherlands.

*Primary Examiner*—Michael J. Milano
*Attorney, Agent, or Firm*—Vidas, Arrett & Steinkraus

[57] ABSTRACT

A temporary stent comprises a coil of tubular thermoplastic material and a heating element inside the tubular material, or a film with a metal film resistive heating element coated thereon. A method of temporarily supporting the wall of a vessel comprises the steps of inserting a thermoplastic body having a first outer dimension less than the inside dimension of the vessel into the vessel to the desired support position; heating the thermoplastic above its softening transition temperature and expanding it to a second outer dimension larger than its first outer dimension; cooling the thermoplastic body to below its softening transition temperature while at its second outer dimension; allowing the cooled thermoplastic body to temporarily support the vessel; heating the thermoplastic above its softening transition temperature to soften the thermoplastic; and removing the softened thermoplastic body from the vessel.

5 Claims, 7 Drawing Sheets

U.S. PATENT DOCUMENTS

| | | |
|---|---|---|
| 5,215,450 | 6/1993 | Anderhub . |
| 5,226,888 | 7/1993 | Arney . |
| 5,231,989 | 8/1993 | Middleman et al. . |
| 5,242,451 | 9/1993 | Harada et al. . |
| 5,250,069 | 10/1993 | Nobuyoshi et al. . |
| 5,252,159 | 10/1993 | Arney . |
| 5,256,146 | 10/1993 | Ensminger et al. . |
| 5,290,229 | 3/1994 | Paskar . |
| 5,354,263 | 10/1994 | Coll ............... 604/8 |
| 5,380,270 | 1/1995 | Ahmadzadeh ............... 604/8 |

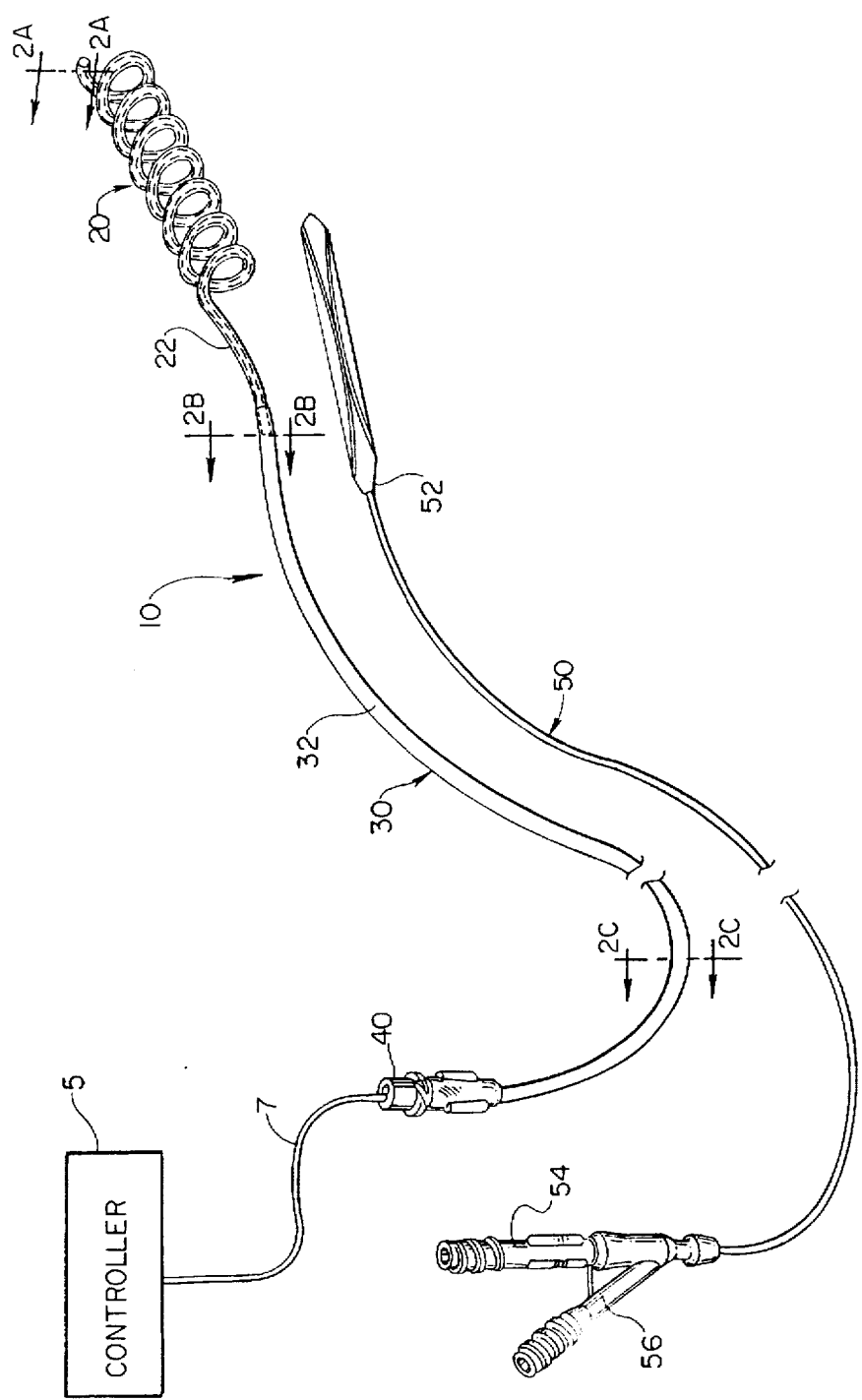

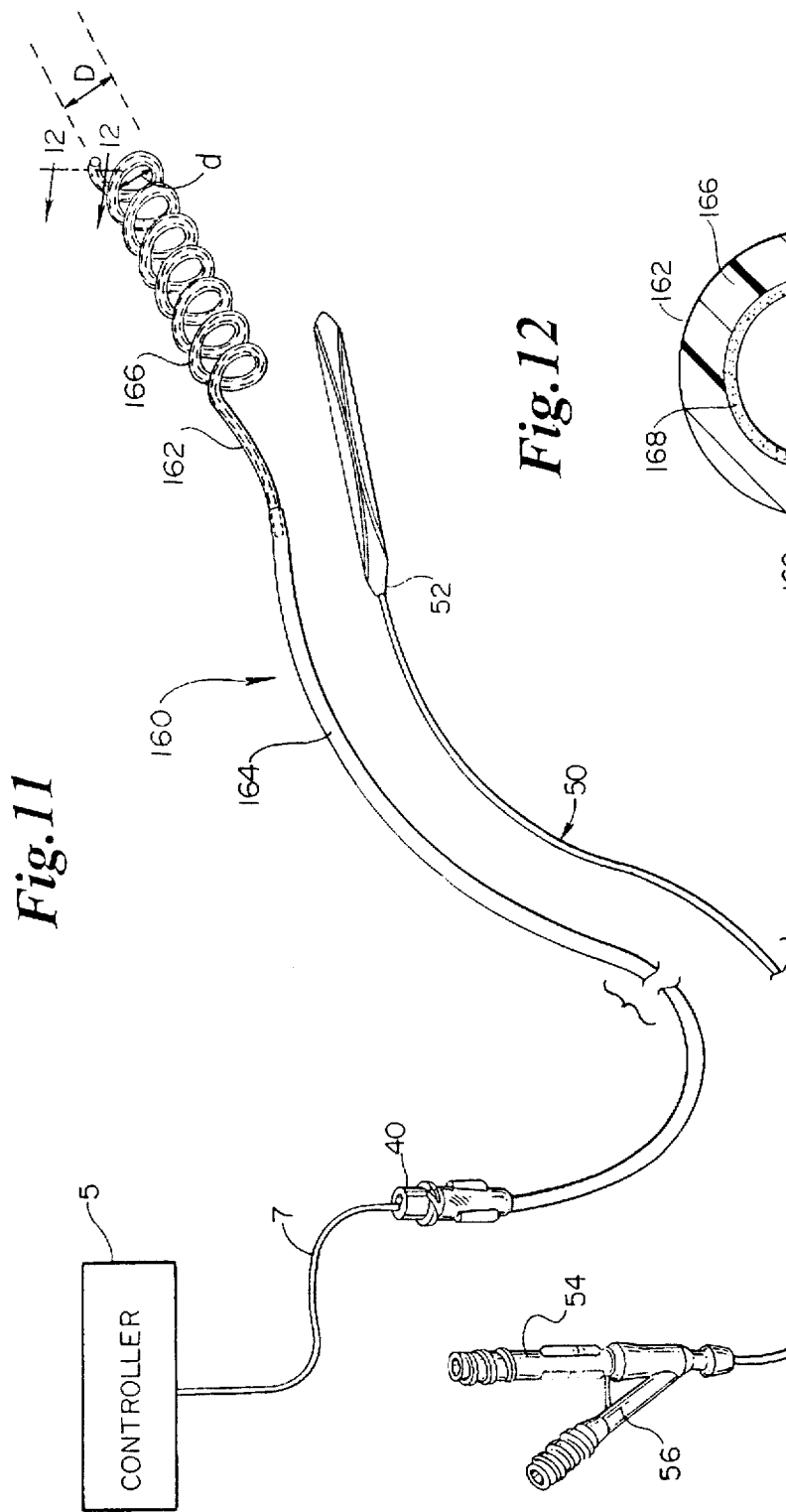

*Fig.13*
*Fig.14*
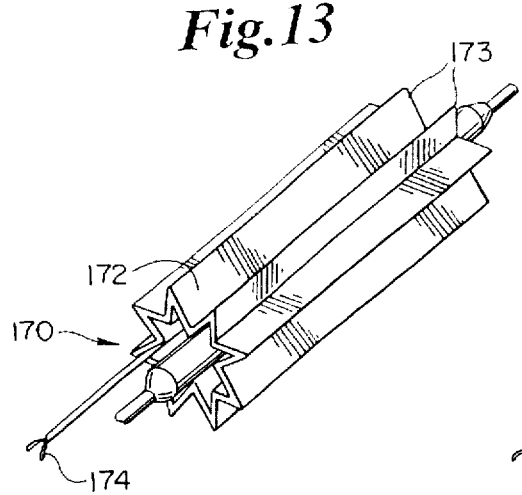
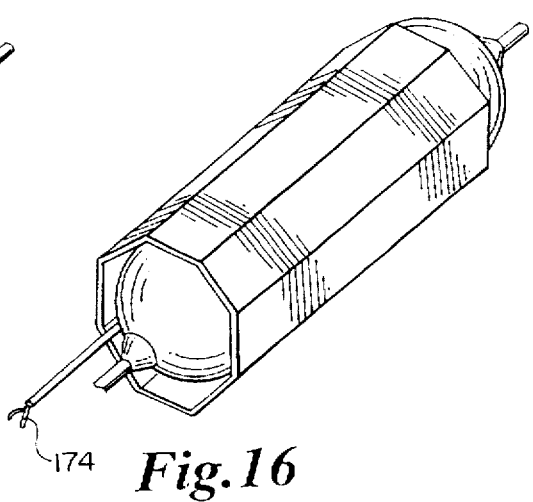
*Fig.15*
*Fig.16*
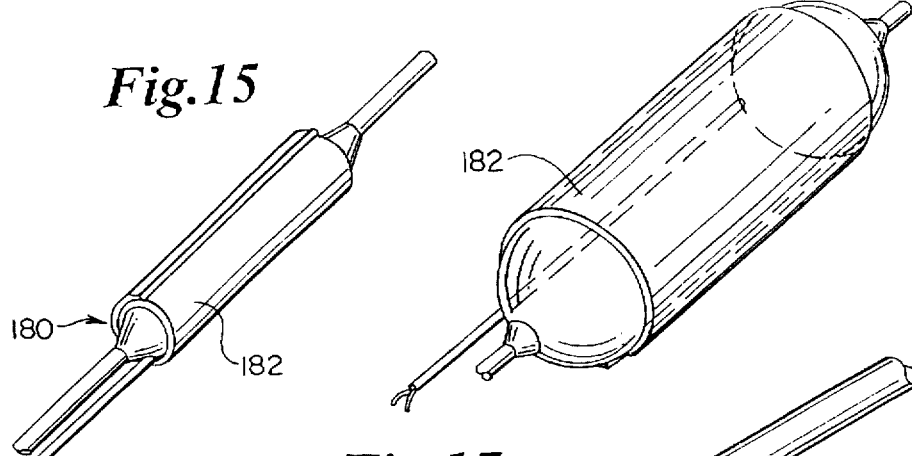
*Fig.17*
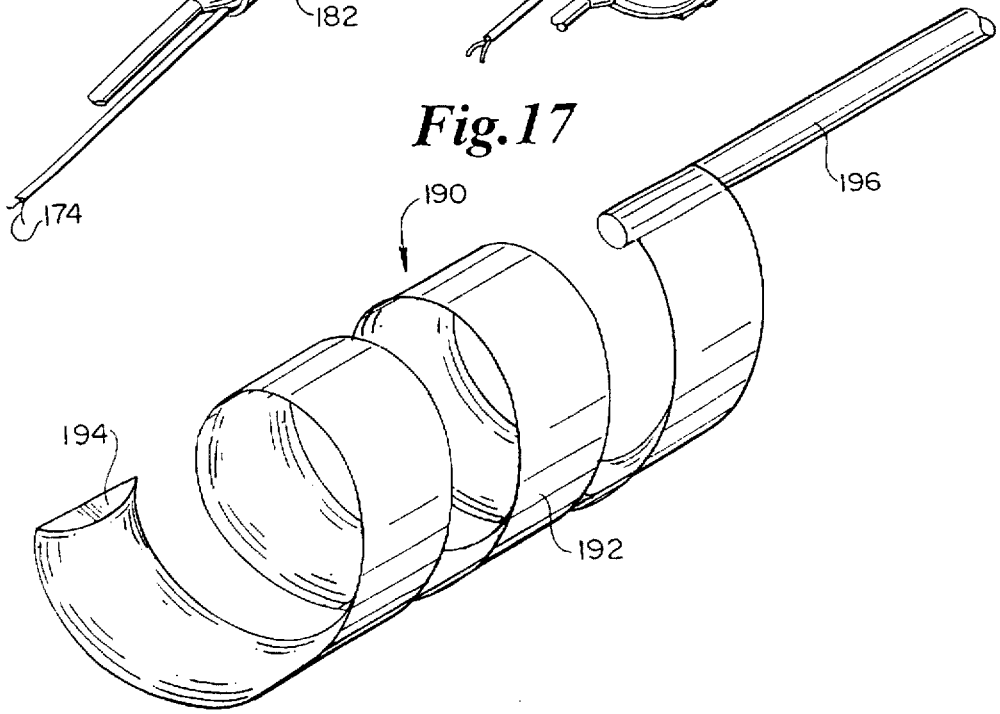

METHOD FOR DELIVERING DRUGS TO A VASCULAR SITE

CROSS-REFERENCE TO RELATED APPLICATION

This application is a file wrapper continuation of U.S. patent application Ser. No. 08/471,653 file Jun. 6, 1995, abandoned, which is a division of 129,860 filed Sep. 30 1993, now abandoned, which is a continuation-in-part of application Ser. No. 08/055,635, filed Apr. 30, 1993, now abandoned the disclosure of which is hereby incorporated by reference.

BACKGROUND OF THE INVENTION

This invention relates to devices known as stents which provide support to a vessel, such as a blood vessel, and in particular to stents that are both temporary and removable.

Obstructive coronary artery disease is one of most serious health problems facing our society today. This disease is the result of the deposit of fatty substances on the interior surface of the walls of the arteries. The build up or lesion of such deposits results in a narrowing of the diameter of the artery which restricts the blood flow through the artery. This condition wherein the artery is narrowed is known as stenosis. The lesion may form in any part of the artery and in some instances the deposits may form at the intersection between two arteries, that is, where the section where the two arteries form a generally "Y" configuration (e.g. bifurcate, trifurcate, and so on).

There have been significant developments of the treatment of such obstructive coronary disease in the recent past. Coronary artery bypass graft surgery is often used to treat this disease. Bypass surgery, however, has the disadvantage that it is extremely invasive and traumatic to the patient. Some of the recent developments provide a less invasive and less recent developments are known as angioplasty and atherectomy procedures.

Angioplasty is a procedure in which a balloon is positioned on the inside of the artery at the site of the lesion and expanded in order to compress the materials at the lesion and thus open the restricted area in the artery. In this procedure, an elastic balloon is attached to one end of a small diameter flexible catheter which includes means for inflating the balloon from the other end of the catheter. The catheter is maneuvered through the patient's vessels to the site of the lesion with the balloon in uninflated form. When the uninflated balloon is properly positioned at the lesion, the balloon is then inflated to dilatate the restricted area.

Atherectomy is a procedure in which a small cutting tool is attached to the end of a small diameter flexible catheter and maneuvered through the patient's arterial system to the site of the lesion in the diseased artery. When the cutting tool is properly positioned, the tool is used to cut and remove the deposits from the surface of the diseased artery.

Although these two procedures provide less traumatic alternatives to bypass surgery, they are not without risk. It is possible that following procedures such as angioplasty or atherectomy the artery or blood vessel may collapse or be susceptiable to constriction. In some instances it may also be necessary to abort or "bail-out" from procedures such as angioplasty or atherectomy due to some type of unexpected complication.

In these situations it is necessary to maintain the integrity of the region of the artery until the artery is repaired or stabilizes. That is, following some angioplasty or atherectomy procedures or in a "bail-out" situation, it may be necessary to provide support to a artery or blood vessel on a temporary basis while there is an immediate risk that the region may collapse. This support must be provided until the region is repaired or stabilized. To provide this support, a device known as a stent may be installed at the desired region. A stent is a device which is used to hold or maintain the diameter of the artery or vessel.

Although some stents are available in the art, these are generally of the type intended for permanent use. This type of permanent stent is implanted in a patient's vascular system and remains in place after the procedure or operation. Such permanent types of stents are shown, for example, in U.S. Pat. Nos. 4,913,141; 4,878,906; 4,856,516 and 4,820, 298. These permanent type of stents may not always be desired for the situations described above. First, it may be unnecessary and even undesirable to install a permanent device when only temporary support is needed. Further, these permanent type of stents may require a relatively complicated procedure to install. Further, use of permanent stents results in extended hospital observation and recovery time. Additionally, a complement of drug therapies is required in order to offset the bioreaction resulting in thrombus formation or smooth muscle cell proliferation on the stent surface. These drug therapies may be required for a significant period of time until new normal endothelial cells have formed. In situations such as a "bail-out" it is desirable for the physician to have the ability to quickly maneuver the stent to the desired location and quickly and easily place the stent in its operating mode.

A temporary stent on the other hand may be particularly useful in situations where it is intended to be used in the patient only for several minutes or days and then removed. For example, use of a temporary stent in a bail-out situation will enable the physician to defer a more complicated procedure until a patient's condition is more stable, or in some cases eliminate further procedures by resecuring the vessel geometry to allow near normal blood flow.

A temporary stent may have particular usefulness in situations such as when an intimal flap is encountered, or during occurrences of vasocontriction or vasospasm, or in situations in which there is a potential for such conditions to occur such as following angioplasty. An intimal flap occurs when a portion of the vessel wall partially or completely tears off and hangs down into the blood flow path. An intimal flap may occur during or after an angioplasty procedure. If the flap is large, it may entirely occlude the vessel lumen. The flap may heal itself if it can be maintained in place against the vessel from which it tore.

Vasoconstriction or vasospasm also may occur during or after angioplasty. Vasoconstriction or vasospasm in many cases may accompany the occurrence of an intimal flap, but in many other cases, vasoconstriction or vasospasm may occur independent of an intimal flap. During vasoconstriction or vasospasm, muscles around the vessel contract and can partially or completely occlude the vessel. If the vessel can be maintained open, vasoconstriction or vasospasm may cease after a period of time. Medicines may be administered to treat the vasoconstriction or vasospasm. Whereas a small force may be sufficient to maintain an intimal flap against the vessel wall and maintain blood flow, a significantly greater force would usually be needed to keep a vessel open during an episode of vasoconstriction or vasospasm.

Since the temporary stent remains in place for a period of time, it is important that the temporary stent not block the flow of blood through the vessel. That is, the blood must be able to travel through the vessel in which the temporary stent is installed while the stent is in place. Further, since the lesions often occur at the intersection of two vessels, in order to position the temporary stent it may be necessary to place the stent across the intersection. Therefore, it is important that the stent provide a flow path radially as well as axially or longitudinally. This arrangement will allow blood flow to both of the intersecting arteries.

It is also desirable to have the ability to deliver medicines to the vessel at the placement position of the stent, as well as either upstream or downstream of the temporary stent while the stent is in place.

Since the temporary stent will be removed after a period of time, it is important that the temporary stent not permanently adhere to the inner walls of the vessel in which it is placed. In addition, a temporary stent should have no tendency, or only a minimal tendency, to cause clotting.

Some temporary stents have been disclosed in previously issued U.S. Patents, such as U.S. Pat. No. 4,998,539 to Delsanti, U.S. Pat. No. 5,002,560 to Machold et al. and U.S. Pat. No. 5,034,001 to Garrison et al. The temporary stents disclosed in these patents are very similar, and generally comprise a netting of interlocked wires coupled with a mechanical actuation mechanism. The mechanical actuation causes the wires to bend outward to comprise a stent, or collapse inwardly for removal. Garrison et al. also suggests that the wires could be made of shape memory alloy and heated to cause them to change shape. U.S. Pat. No. 5,037,427 to Harada et al. discloses a stent made of a two-way shape memory alloy that expands and shrinks in a radial direction depending on changes in temperature.

One drawback of these disclosed stents is their rather complicated mechanical nature. It is preferable that a temporary stent be easy to construct, and essential that a temporary stent be relatively easy both to install and remove.

A temporary stent providing these features and avoiding the above noted problems is very desirable.

SUMMARY OF THE INVENTION

A temporary stent and methods of use have been invented which allow quick placement at a desired location as well as easy withdrawal of the stent.

In one aspect, the invention is a stent comprising thermoplastic tubing containing a heating element inside the thermoplastic tubing.

In a second aspect, the invention is a temporary stent for supporting a region of a patien's vessel comprising an elongate shaft having a proximal end and a distal end and a stenting portion connected to the distal end of the elongate shaft, the stenting portion comprising thermoplastic material configured such that at body temperature the stent portion provides vessel support, and at an elevated temperature less than 100° C. the stenting portion may be reconfigured from the support configuration to a configuration that may be transluminally withdrawn from the vessel.

In another aspect, the invention is a stenting apparatus comprising a coil of tubular thermoplastic material at the distal end of the apparatus; an electrical resistance heating element within the tubular material; a catheter shaft extending from the distal end to the proximal end of the apparatus; electrical conductors within the shaft for conducting electrical current to the resistance heating element; and an electrical connector at the proximal end of the apparatus for connecting the conductors with a source of electrical current.

In yet another aspect, the invention is a method of temporarily internally supporting a patient's vessel comprising the steps of transluminally deploying a stent to support the vessel, the stent being connected to a member that extends at its proximal end out of the patient; heating the stent to allow it to take a configuration different than its configuration when it supports the vessel; and pulling on the connecting member to remove the stent.

In still another aspect, the invention is a method of temporarily stenting a vessel comprising the steps of deploying a thermoplastic stent transluminally into the vessel, the stent comprising a tube with an electrical heating element inside the tube and the tube being configured to form a stent; applying current to the heating element to generate heat and thereby soften the thermoplastic; expanding the stent to a desired support dimension; allowing the stent to cool and remain in its support dimension; applying current to the heating element to generate heat and thereby soften the thermoplastic so that it can be deformed to a dimension suitable for removal from the vessel; and removing the stent from the vessels.

Other aspects of the invention relate to a method of removing a temporary stent, a method of heating a stent, an expandable ballon catheter with a coil of thermoplastic tubing wrapped around the balloon, and a method of making a stent from an elongated member.

In a preferred aspect, the invention is a method of temporarily supporting the walls of a vessel comprising the steps of inserting a thermoplastic body having a first outer dimension less than the inside dimension of the vessel into the vessel to the desired support position; heating the thermoplastic above its softening transition temperature and expanding it to a second outer dimension larger than its first outer dimension; cooling the thermoplastic body to below its softening transition temperature while at its second outer dimension; allowing the cooled thermoplastic body to temporarily support the vessel; heating the thermoplastic above its softening transition temperature to soften the thermoplastic; and removing the softened thermoplastic body from the vessel.

With this arrangement, the temporary stent may be positioned in the desired region and may be used to maintain vessel patency during the occurrence of an intimal flap, vasoconstriction, vasospasm, or other conditions that occlude the vessel lumen or when there is a potential that such conditions may occur such as following angioplasty. With the preferred embodiment of the invention, the stent may be quickly and easily deployed. Blood can flow through the stent while the stent is in place. When the need for the stent has ended, it can easily and quickly be removed.

These and other advantages of the invention, as well the invention itself, will be best understood in view of the attached drawings, a brief description of which follows.

BRIEF DESCRIPTION OF THE DRAWINGS

FIG. 1 depicts a first embodiment of the present invention.

FIG. 11 depicts a sixth embodiment of the invention.

FIG. 12 is a cross-sectional view taken along line 12—12 of FIG. 11.

FIGS. 13 and 14 depict a seventh embodiment of the invention in a deployment and expanded position, respectively.

FIGS. 15 and 16 depict an eighth embodiment of the invention in a deployment and expanded position, respectively.

FIG. 17 depicts a ninth embodiment of the invention.

DETAILED DESCRIPTION OF THE DRAWINGS AND PREFERRED EMBODIMENTS OF THE INVENTION

Figure 2A:
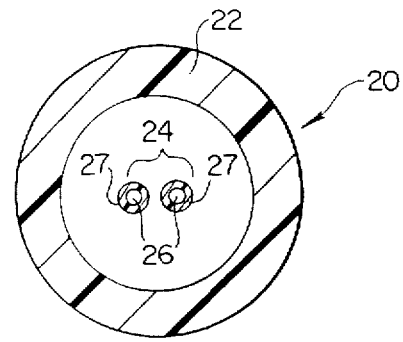
FIG. 2A is a cross-sectional view taken along line 2A—2A of FIG. 1.

A first embodiment of the invention, depicted in FIG. 1, is a stenting apparatus 10. The apparatus 10 includes, at is distal end, a thermoplastic body 20 forming the stent portion of the apparatus, a catheter shaft 30 and an electrical connector 40 at its proximal end. Preferably the thermoplastic body 20 is in a coiled form, having a length L and an outer diameter D, the length L being greater than the outer diameter D. Also shown in FIG. 1 is a standard balloon catheter 50, having a balloon 52 at its distal en and typical connectors 54 and 56 at its proximal end for inflating the balloon 52 and providing a guide wire insertion lumen, as is well known in the art and therefore not further discussed herein. FIG. 1 also shows wires 7 running from the electrical connector 40 to a controller 5, discussed below.

As shown in FIG. 2A, the thermoplastic body 20 comprising the temporary stent of the first embodiment is made of a tubular member 22. Preferably the tubular member 22 is made of heat softenable, thermoplastic material and contains an electrical resistance heating element 24 within the tubular member 22. The electrical resistance heating element 24 is a resistance wire 26 covered by insulation 27. The wire 26 doubles back so that both of its ends are proximal to the thermoplastic body 20, which is why two wires 26 are seen in the cross section of FIG. 2A. Preferably the wire 26 is in the form of bifilar silver wires that are electrically joined at an end near the distal end of the thermoplastic body 20.

Figure 2B:
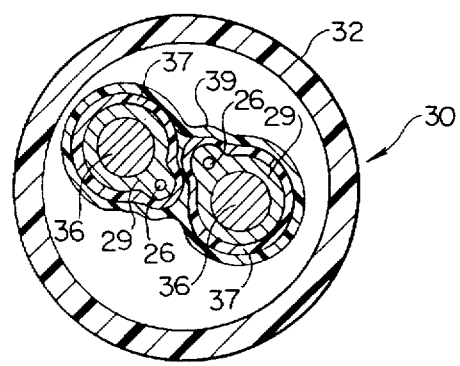
FIG. 2B is a cross-sectional view taken along line 2B—2B of FIG. 1.
Figure 2C:
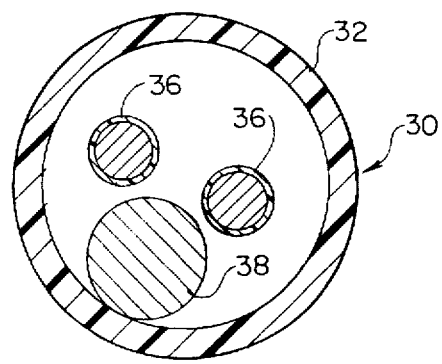
FIG. 2C is a cross-sectional view taken along line 2C—2C of FIG. 1.

The catheter shaft 30 is a hollow member 32 carrying two electrical conductors 36, each in the form of insulated wires, as best seen in FIG. 2C. Over most of its length, the catheter shaft 30 further contains a mandrel 38 to provide rigidity and strength to the catheter shaft 30.

The catheter shaft 30 is slightly larger in diameter than the tubular member 22, and, as shown in FIG. 1, the tubular member 22 fits inside the hollow member 32 about one-fourth inch. Just proximal from the point that the tubular member 22 and hollow catheter shaft member 32 join, the conductor wires 36 are soldered to the proximal ends of the wire 26. As seen in FIG. 2B, the solder 29 surrounding each junction is covered by shrink wrap film insulators 37, and both junctions are held together by another shrink wrap insulator 39 surrounding the insulators 37.

The preferred electrical resistance heating element 24 is one that is made of wire 26 for which the resistance of the wire 26 is strongly and linearly dependent on the temperature of the wire 26. Due to this characteristic, the temperature of the heating element 24 can be easily monitored by monitoring the resistance of the wire 26. The controller 5 can then use the resistance as a feedback control in regulating the current applied to the conductors 36 and hence wire 26, to control the temperature of the wire 26 based on a desired set point temperature. The details of a preferred controller 5 and its use in heating wire 26 are disclosed in U.S. patent application Ser. No. 08/055,702, filed Apr. 29, 1993 entitled "Apparatus and Method for Performing Diagnostics and Intravascular Therapies", the disclosure of which is hereby incorporated by reference.

In the embodiment of FIG. 1, it is preferable that the thermoplastic body 20 be made of a material that has a shape memory property. Such materials are well known, and many thermoplastic polymers have some shape memory properties. That is, the material may be coiled and set in a first shape, and thereafter deformed. When the material is heated to its shape memory activation temperature, which is normally its glass transition temperature, the material will return to its first shape unless constrained. For the embodiment of FIG. 1, it is preferable to use a material with a sharp shape memory/glass transition temperature above normal body temperature (37° C.) but within the range that is tolerable by the blood vessels (100° C.). A preferred temperature range is between about 40° C. and about 80° C.

When the stent portion of apparatus 10 is made from a highly amorphous polymer, it is produced by helically coiling a polymer tube 22 and then heating it to a temperature well above the glass transition temperature of the polymer to "set" the shape. Depending on the shape memory material used, the material may be heated to between 80° C. and 150° C. for a period of one second to one hour. The shape is that of the helical coil having an outer diameter equal to that desired for the stent when it is in a support position. Thereafter, at a lower temperature, slightly above the glass transition temperature, the coil is "tightened" down by adding some additional turns, thereby reducing its outer diameter to the size necessary for transluminal placement. Preferably the inner diameter of the helix is such as to provide a snug fit on a balloon 52.

Figure 3:
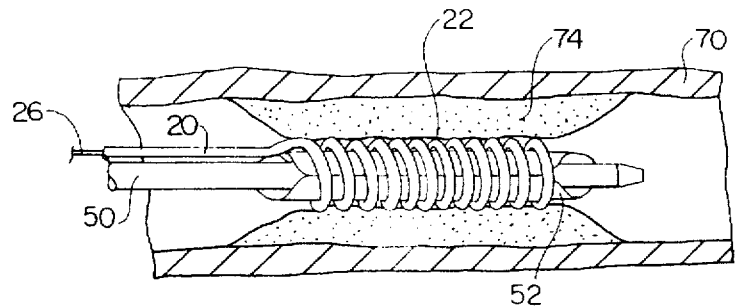
FIGS. 3–6 are representations of the stent of the embodiment of FIG. 1 in the positions, respectively, of deployment, expansion, balloon removal and stent removal.

As shown in FIG. 3, the temporary stent 22 is delivered on a balloon 52 to a portion of artery 70 for desired placement. That could be an area where balloon angioplasty was previously performed, or, as shown in FIG. 3, a place where there is an obstruction 74 in the artery that is still to be treated.

Figure 4:
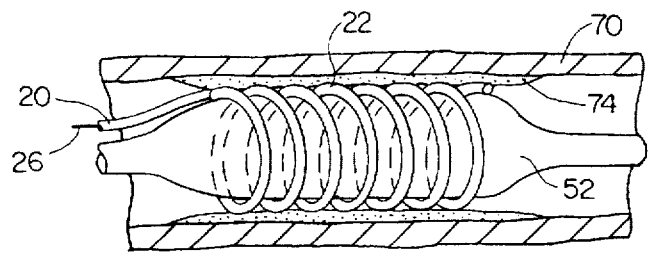

Once the stent 22 is in place, the controller 5 is turned to an "on" position and current is transmitted from the controller 5, through wires 7 (FIG. 1), electrical connector 40 and conductors 36 to wires 26, resulting in resistance heating of tubular material 22. Once the tubular material is heated above its glass transition temperature, it will attempt to return to its "set" larger diameter. At this point, balloon 52 may be inflated to expand the stent 22 as well as to unblock artery 70 (FIG. 4).

Figure 5:
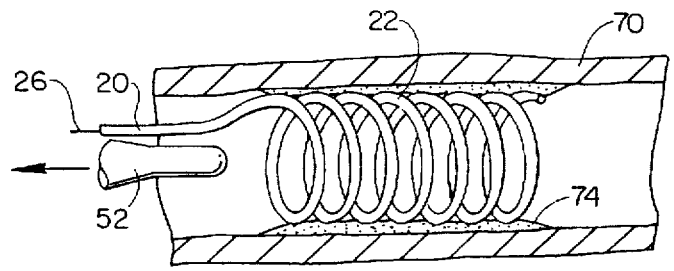

Once the stent 22 is in its support position, the controller 5 is turned off and the thermoplastic material of stent 22 is allowed to cool. As the stent 22 cools, the thermoplastic material becomes rigid, meaning that it is stiff enough to prevent collapse of the vessel wall. Thereafter, the balloon 52 may be deflated and withdrawn (FIG. 5).

The stent 22 remains in artery 70 for the time period desired by the medical personnel involved which may range from a few minutes to as long as a week. During this period, the catheter shaft 30 traverses the vascular system and extends at its proximal end out of the patient. Of course, the electrical connector 40 may be disconnected from wires 7 if the period of placement is sufficiently long.

Figure 6:
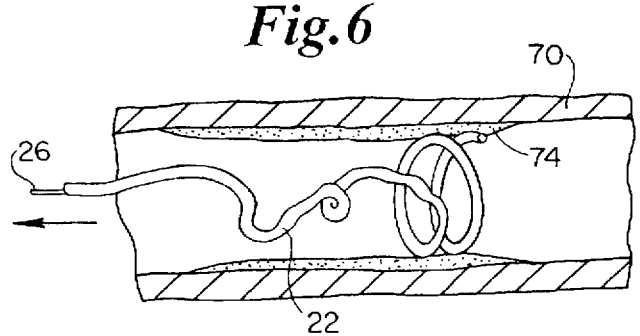

When it is time to remove stent 22, controller 5 is again used to apply current to the heating element 24 to generate heat and thereby soften the thermoplastic so that it can be deformed to a dimension suitable for removal from the vessel 70. In its heated state, the thermoplastic is soft and flexible. As shown in FIG. 6, where the thermoplastic body 20 is in the form of a coil, the coil is deformed by pulling on catheter shaft 30. The catheter shaft 30 thus serves as a connecting member to remove the stent 22. As the catheter shaft 30 is pulled, the stent 22, being softened, uncoils or unwinds to a very low profile tube and can be removed from the artery 70.

Figure 7A:
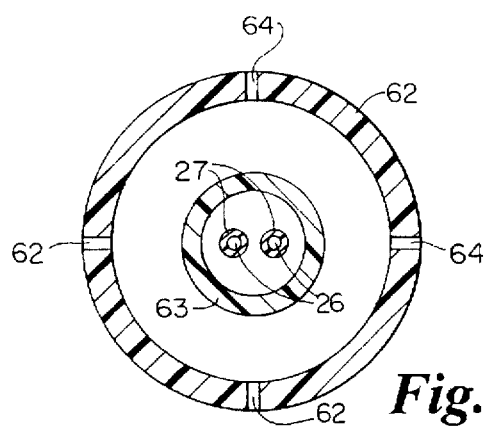
FIG. 7A is a cross-sectional view like FIG. 2A of a second embodiment of the invention.

If it is desired to inject drugs to the tissue surrounding the stent 22 during the time it is in place, then the tube 22 may be altered. FIG. 7A shows a second embodiment where the thermoplastic body again is in the form of a tube 62. The side walls of the tube are provided with holes 64 spaced and sized so as to allow drug delivery through the tube wall. It may then be preferable, as shown in FIG. 7A, to encase the insulated wires 26 in a separate lumen 63 to isolate them from the drug delivery flow path. Such a separate lumen may be provided, in yet another embodiment shown in FIG. 7B, by extruding tube 82 together with internal wall 83. The holes 84 are then provided in the sides of tube 82 in fluid communication with the main portion of tube 82. In drug delivery embodiments of the invention, it may be preferable to use a tube 22 with a cross-section having a flat side, which will be in contact with the arterial wall when the tube 22 is formed into a stent and expanded into place.

More preferred embodiments of the thermoplastic body are shown in FIGS. 8A, 8B, 10A and 10B. In these figures, the thermoplastic body is formed into coils of different designs. Each coil has a length L greater than its outer diameter D. The coils shown in these figures are preferable because the coils are radially expandable as well as heat softenable. While the coils may be formed of shape memory material, the radial expendability of the coils, by their design, makes it unnecessary to first form the coils into a larger diameter at a set shape. Since other elements of the invention are the same, reference numbers used in FIGS. 8A, 8B, 10A and 10B are the same as corresponding elements in FIGS. 1–6.

Figure 8A:
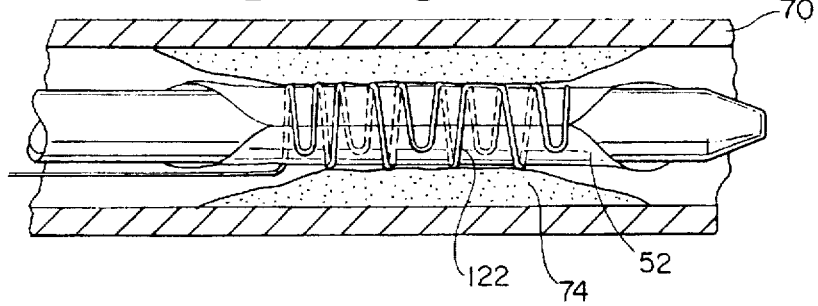
FIGS. 8A and 8B are representations like FIG. 3 and 4 of a fourth embodiment of the invention.
Figure 8B:
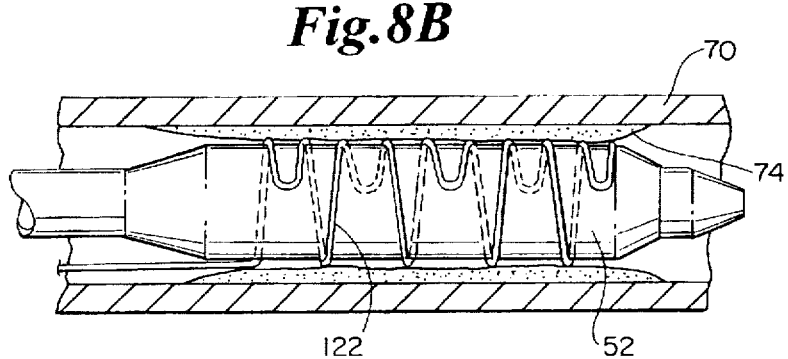

FIG. 8A shows a stent coil 122 made of reversing loops. The stent 122, like stent 22 preferably is made of a tubular material that contains an electrical resistance heating element. In fact, other than the shape of the coil, the stent apparatus of FIGS. 8A and 8B is the same as the stent apparatus 10 of FIG. 1. When the stent 122 is heated and softened, the balloon 52 can expand the stent 122 radially without the need for the thermoplastic to first return to a previously set shape. This is because the reversing loops allow the radial expansion of the coil without the coil having to unwind around the entire length of the stent, as required with the helical coil stent of FIG. 1.

Figure 9:
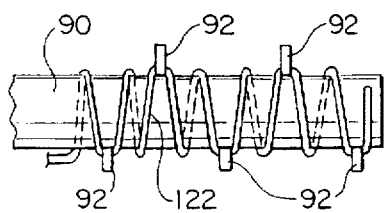
FIG. 9 is a representation of a mandrel used to form the stent coil of the embodiment of FIGS. 8A and 8B.

The reversing loop coil of FIGS. 8A and 8B can be formed on a mandrel 90 as shown in FIG. 9. The mandrel 90 has a generally cylindrical shape and removable cross pieces 92 protruding radially along the length of the mandrel 90. A tube (or other elongated member if the stent is heated without the need of internal resistance wires) is wound around the circumference of the mandrel 90 in a first direction starting at one end and moving toward the other end of the mandrel 90. When it is desired to reverse the direction of the coil, the elongated member is looped over one of the removable cross pieces 92 as shown in FIG. 9, and winding of the elongated member is continued in a circumferential direction opposite the first direction, but in the same longitudinal direction down the mandrel 92. The process of looping the elongated member over a cross piece 92 is repeated and the winding in the different directions is repeated until the stent 122 is of desired length. The preferred coil reverses every 1½ turns, or 540°. However, coil reversals could occur at intervals up to 1080° and as low as 180°. The coils need not be uniform. For example, the elongated member could be wound 2½ turns in one direction, 1 turn in the opposite direction, ¾ of a turn in the first direction, and so on.

After the winding is completed, the cross pieces 92 are removed from the mandrel 90 and the reversing loops can be slid off the mandrel 90. The elongated member may be heated to soften it while it is being wound and then allowed to cool and become stiff or rigid on the mandrel, or the elongated member may be wound with sufficient force to elastically deform the material and then held in place on the mandrel 90 while it is heated to relx the elastic deformation and a cooled to become rigid.

Figure 10A:
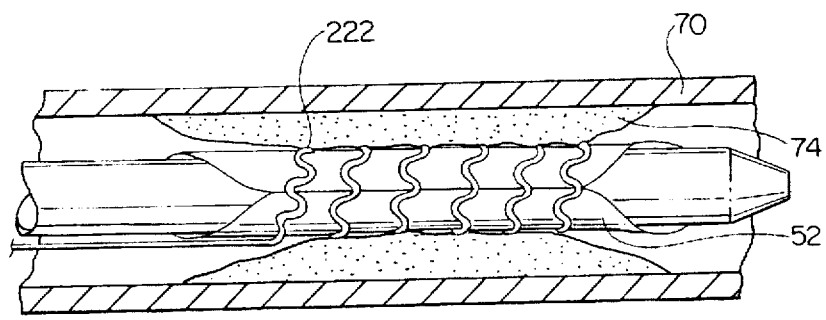
FIGS. 10A and 10B are representations like FIGS. 3 and 4 of a fifth embodiment of the invention.
Figure 10B:
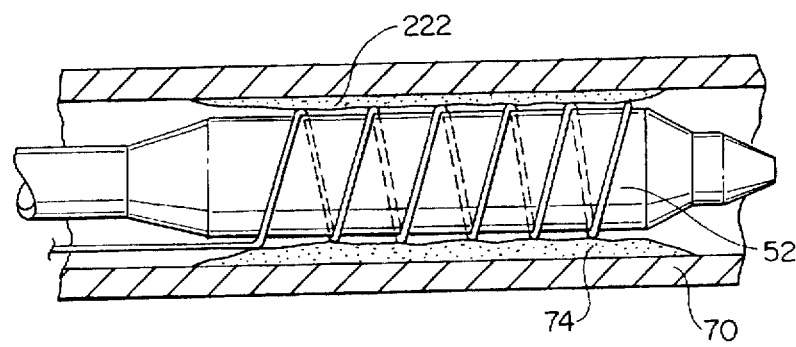

FIGS. 10A and 10B show a second embodiment of a radially expandable coil formed into a stent 222. Like the embodiment of FIGS. 8A and 8B, the stent 222 is preferably used with the stenting apparatus of FIG. 1. However, the thermoplastic body in this embodiment is in the form of a zig-zag coil. In the zig-zag coil, the individual loops of the coil include curving sections that allow the coil to radially expand by straightening out the curving sections, as shown in FIG. 10B.

The stents 122 and 222 of FIGS. 8B and 10B can be removed from the vessel 70 in the same fashion as stent 122, by pulling on the connecting catheter shaft 30 after heat has been applied to soften the thermoplastic material.

The thermoplastic material is preferably a highly amorphous polymer. In the preferred embodiments, the stents 22, 122 and 222 are made from polyurethane, such as the SMP series of polyurethane from Mitsubishi. The MM-4500, MM-4510 and MM-4520 polyurethanes have a glass transition temperature of 45° C., and are particularly preferred. The MM-5500, MM-5510, and MM-5520 polyurethanes have a glass transition temperature of 55° C., and will also work well. As used herein and in the claims, the glass transition temperature for highly amorphous thermoplastic polymers and semi-crystalline thermoplastic polymers is referred to generically as the softening transition temperature of the material.

In the preferred embodiments, the tubular material 22 is made using convention extrusion processes to make an extruded tube with an inside diameter of about 0.011 inches and an outside diameter of about 0.021 inches. Where Mitsubishi MM-4500 polyurethane is used, the extruded tubing is then heated to about 100° C. to form the coil. The tubing is then cooled to room temperature and reheated to between 55° C. and 60° C. to be deformed into a smaller diameter coil, the smaller diameter coil having an inside diameter of about 0.031–0.033 inches (to provide a snug fit on a folded balloon 52) and an outer diameter of about 0.060 to 0.070 inches, which is small enough to be transluminally inserted into a coronary artery. Where the stent is used on peripheral arteries, the preferred size of coil will be larger. Of course, if the shape memory aspect of the polymer is not needed, as with the embodiments of FIGS. 8–10, the extruded tubing is heated only to a temperature at which it softens and is directly formed into the small diameter coil.

The preferred catheter shaft 30 is made from polyethylene tubing 32 having an inside diameter of 0.030 inches and an outside diameter of 0.035 inches. It may be glued to the tubing 22 by HP Fuller UR 3507 (two part) adhesive. The tube 22 preferably joins to catheter shaft tube 32 about ¼ inch from the beginning of the coil turns.

The mandrel 38 is preferably a steel wire of about 0.012 inches in diameter. The mandrel 38 preferably ends about two inches from the junction of the catheter shaft tube 32 and tubing 22.

The preferred heating wire 26 is bifilar silver wire; 0.001 inches in diameter, covered by insulation about 0.0001 inches thick. Heating wires in the range of about 0.0005 inches to about 0.003 inches are suitable. The preferred conductor wires 36 are silver wires each 0.006 inches in diameter, however wires from about 0.003 to about 0.01 inches are suitable. The wires 26 and 36 are preferably soldered and insulated as shown in FIG. 2B about 1½ inches from the distal end of the catheter shaft tube 32.

The controller 5 preferably provides an AC current of about 25 kHz to the resistance heating element 24. The electrical resistance of the heating element 24 is preferably in the range of 2–20 ohms at room temperature. As described previously, the controller 5 preferable provides a temperature-dependant current to the heating element, preferably in the range of 0 to 1 amps. Preferable the stenting apparatus 10 will be constructed in a manner such that different devices will all have the same resistance and temperature/resistance relationship, and then the controller 5 can be set up once and used repeatedly without being calibrated for different devices. Where a Mitsubishi MM-4500 polyurethane is used for the stent, the wires 26 are heated to about 50° to 55° C. to soften the stent 22 when it is in place in the artery ready to be expanded or withdrawn.

Figure 7B:
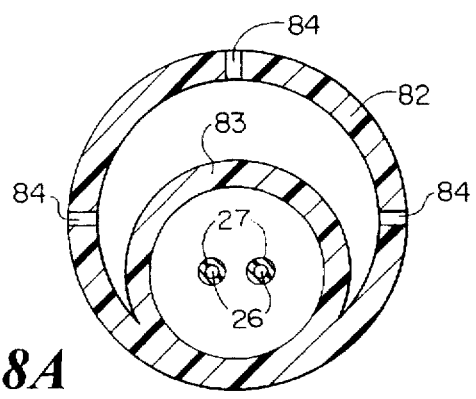
FIG. 7B is a cross-sectional view like FIG. 2A of a third embodiment of the invention.

Instead of holes 64 and 84 shown in FIGS. 7A and 7B, the tubing material can also be made of a semi-permeable membrane to allow drug delivery through the tubing 22.

Because the stent 22 contains electrical wire 26, it is possible to use the stenting apparatus 10 to practice iontophoresis in addition to heating the stent. Iontophoresis is the process of causing a drug to enter tissue by making the drug electrically charged and the surrounding tissue oppositely charged. The use of a balloon tube to infuse an electrically charged, solution at a desired spot in the body is described in U.S. Pat. No. 5,047,028 to Qian, incorporated herein by reference. The process of iontophoresis is described in more detail in U.S. patent application Ser. No. 07/520,033, filed May 7, 1990, entitled "Method and Apparatus for Inducing the Permeation of Medication Into Internal Tissue," hereby incorporated by reference.

To use the stenting apparatus 10 to practice iontophoresis, a portion of the insulation 27 on wire 26 (FIG. 2A) is removed so that a voltage can be applied between wire 26 and an electrode attached to the outside of the patient's body. The tubular material 22 will contain holes, possibly only microscopic pores, that allow migration of drug ions from the stent to surrounding tissue upon application of a voltage applied between the wire 26 and the tissue via the electrode on the patient's body.

While tubing 22 formed into coils constitutes the preferred embodiment of the invention, the temporary stent can be formed from other materials and shapes. The important feature is that the thermoplastic body be formed so that it can be expanded from a shape having a first outer dimension less than the inside dimension of the vessel to a second outer dimension larger than its first outer dimension, and that after the stenting is completed, the thermoplastic body may take on a configuration different than its support configuration, such as a dimension suitable for removal from the vessel. Most preferably, when the stent is treated, such as by heat, the stent is allowed to form an elongated, pliable member. Then the stent can be removed by pulling, starting at one end, the elongated, pliable member transluminally from the artery.

While internal heating of the thermoplastic body in the form of a tube 22 is preferred, it is recognized that heating may be accomplished in other ways, and that the thermoplastic body need not be tubular and need not contain an electrical resistance heating element. For example, the stent 22 could be heated by a balloon 52 that is appropriately equipped, such as disclosed in U.S. patent application Ser. No. 08/055,702, and a heating balloon or some other heating element could be reinserted into the stent when it was desired to remove the stent. For example, if the coil were made of a tube that reversed back on itself, so that after ends were proximal of the body, warm fluid could be pumped through the tube when it was desired to heat the thermoplastic material.

A sixth embodiment of the invention is shown in FIG. 11. The stenting apparatus 160 comprises a stent portion 162 and a connecting tube 164. Many portions of the apparatus 160, such as the controller 5, balloon catheter 50 and connections are the same as those shown in FIG. 1, and are marked with the same reference numbers in FIG. 11. The stent portion 162 of the apparatus 160 is made of a polymer with a heat-set memory. In this embodiment, however, the memory shape is a smaller configuration than the support configuration. The stent portion 162 is in the form of a helical coil of tubing 166 the coil having a length L greater then its outer diameter D. The heat-set form is a more tightly wound helical coil.

As shown in FIG. 12, the polymer tubing 166 has a resistive heat element 168 in the form of a thin layer of metal coated on the polymer, preferably on the inside of tubing 166. As with stenting apparatus 10, two wires are provided in the connecting tube 164 to supply electrical current. One of the wires (not shown) terminates at the proximal end of resistive heat element 168. The other wire 169 runs through the coil and connects to the proximal end of the resistive heat element 168.

The stent is deployed by placing it around a balloon 52. Once the stent 162 is in, place in the artery, the stent 162 is heated above its glass transition temperature by ohmic heating. This softens the polymer. The balloon 52 is inflated to expand the stent to its support configuration. The stent 162 is then allowed to cool to below its glass transition temperature, at which time the balloon 52 can be contracted and removed, leaving the connecting tube 164 attached to the stenting portion 162.

When it is time to remove the stent 162, a catheter (not shown) is threaded over the connecting tube 164 and positioned next to the stent 162. Again the stent 162 is heated by ohmic heating. Without the balloon present, the stent 162 shrinks to its previously heat-set configuration when it reaches its glass transition temperature. The stent can then be withdrawn into the catheter and removed from the artery. Alternatively, the stent 162 can continue to be heated and removed in a pliable state, as with the stent 22 shown in FIG. 6.

Almost any thermoplastic polymer that has a glass transition temperature or softening temperature between 40° C.

and 80° C. may be used to form the stent 162. The polymer should have a melt temperature much greater than the glass transition temperature. The preferred material has a glass transition temperature between 40° C. and 55° C. to minimize damage to the arterial wall. The heat-set temperature should be between the glass transition temperature and melt temperature. For example, polyurethanes with a glass transition temperature of 45° C. and a melt temperature of 160°–200° C. may be used. In this case, the set temperature (or annealing temperature) of the polyurethane are between 60° C. and 100° C., preferably 70° C. to 80° C. Polyesters with a melt temperature of above 250° C. would also work. Polymers with these properties can be said to have "memory" by virtue of their crystalline state but this "memory" is not true memory as in nitinol memory metal or thermoset polymers. Polylactide—a biodegradable polyester—with a grass transition temperature of 60° C. is setable at 90° C. A biodegradable polymer may be preferable in that the portion of the stent that degrades while the stent is in place may minimize tissue adhesion.

A preferred material for the stent 162 of FIG. 11 is a Mitsubishi MM4510 polyurethane with a glass transition temperature of 45° C., shaped into a tube.

As shown in FIG. 11, the tubing 166 is wrapped into a helical coil and set, preferably having an outside diameter D of 0.02–0.1 inches and an inside diameter d of 0.01–0.075 inches. When the stent 162 is expanded, the helical coil preferably has an outside diameter D of 0.04–0.16 inches and an inside diameter d of 0.03–0.13 inches. The preferred diameters D and d will depend on the size of the vessel to be stented and the size of the catheter used to deliver the stent. The inside diameter d of the expanded stent provides a lumen which allows blood to easily flow through the stent.

The resistive heat element 162 used to make the stent 152 is preferably nickel oxide or a silicon layer doped with alloys such as germanium. The nickel oxide or the germanium doped silicon oxide acts as a semi-conductor to allow ohmic heating. The coating is in the order of 200 to 2000 Angstroms thick. The coating is preferably deposited by vapor deposition (as taught in U.S. Pat. No. 3,466,229), ion sputtering (as taught in U.S. Pat. No. 5,196,103), or radio frequency plasma sputtering (as taught in U.S. Pat. No. 4,395,313). Other patents disclosing processes for metalizing a polymer surface include U.S. Pat. Nos. 3,267,007; 3,567,487; 3,767,538; 3,847,659; 3,898,136; 4,444,848; 4,568,413 and 5,112,462. Each of the eleven foregoing patents is hereby-incorporated by reference.

Alternatively, a coating of inductive heating material, such as a ceramic glaze that contains carbonyl groups or other polar molecules, could be applied to the tubing 164, which would allow the stent 162 to be heated by inductive heating.

Electroactive polymers, such as those described in *Science*, Vol. 231, pages 25–31 (January 1986) may also be used as the resistive heat element 168. Protective coatings, such as parylene, may be applied to the resistive heat element 168. Parylene coating processes are available from Advanced Surface Technology, Nine Linnell Circle, Bellerica, Mass. 01821-3902 and Specialty Coating Systems, Inc., 5707 West Minnesota Street, Indianapolis, Ind. 41241.

A seventh embodiment of the invention is depicted in FIGS. 13 and 14. In this embodiment, the stent 170 has a "star shape" in its collapsed form. The stent portion 172 is made from material extruded into a thin wall tube with an OD in the range of 3 to 4 mm and a wall thickness of about 0.005 to 0.010 inches. The material is heated above its glass transition temperature and folded into a star shape with three or more arms 173. The arms may be formed by placing the tube over a mold used as a mandrel, with the star shape on the outside of the mold. A vacuum is then drawn on the tube. Especially with the assistance of an outer mold to crimp the polymer, the arms 173 are thus formed. The arms are next folded sideways as the stent is wrapped over a core with an external diameter the size of the uninflated balloon used to deploy the stent. The stent is cooled and then heat set at 60° C. to 90° C. for 6 hours.

The stent uses a resistive layer and wires 174 as with stent 162. The stents is deployed and retrieved in a manner similar to the stent of FIGS. 11–12, except that when it is heated and expanded, the arms 173 come unfolded, as shown in FIG. 14.

An eighth embodiment of the invention is depicted in FIG. 15. In this embodiment, the stent 180 is made from a rolled sheet 182 of polymer. Extruded polyurethane, or polyurethane pressed with a flat press, is made into a sheet about 0.004 to 0.008 inches thick. The sheet 182 is wrapped around a mandrel preferably about 1.5 mm in diameter. The sheet 182 should be wide enough to form 1½ to 2 revolutions around the mandrel. A restraining tube is placed around the sheet and core to keep the sheet from opening up. The sheet is then heat set or annealed for 6 hours or more. The polymer is coated with an ohmic or inductive heating element, and is deployed and withdrawn just as stent 162. FIG. 16 shows the stent 180 in its support configuration.

A ninth embodiment of the invention, shown in FIG. 17, is a stent 190 made from a long, narrow strip 192 of polymer wrapped in a helical fashion. Preferably the cross section 194 of the strip 192 has a tapered shape to permit more laminar blood flow through the center of the stent 190 once the stent is in place in the artery. The stent 190 is made by forming the strip 192, such as by extrusion, and wrapping the strip into a helical shape and connecting it to a connecting tube 196 used to withdraw the stent 190. The stent 190 is preferably coated with a material that allows it to be heated by inductive heating to avoid having a conducting wire traversing along or between the coils. The stent 190 is heat set in a tightly wrapped form.

The stent can be deployed on a balloon catheter as with the other embodiments, heated to soften the strip 192 so that the stent 190 can be expanded on a balloon (not shown), and then cooled in the expanded, support position shown in FIG. 17. When the stent 190 is again heated, it will return to its smaller shape for removal, as with the stents of FIGS. 11, 13 and 15. The strip 192 is preferably about 2 mm wide and 0.005–0.010 inches thick at its maximum thickness.

When electrical current is used for heating, preferably an alternating current is used to avoid biological problems associated with direct current. When inductive heating is used, the frequency of the excitation energy used will be based on the responsive frequency of the material used to form the resistive layer, but will not affect the tissue surrounding the stent. Preferably the frequency will be in the radio frequency range. The poles of the field generator are preferably located in the connecting tubing attached to the stent.

One of the benefits of using one of the coil shapes of FIGS. 4, 8A, 10A, 11 or 17 for the thermaoplastic body is that when the thermoplastic body is expanded to its second outer dimension, the thermoplastic body includes a flow pathway through the thermoplastic body so that blood or other fluid is allowed to flow through the pathway (after the balloon is removed as in FIG. 5) while the thermoplastic body temporarily supports the vessel walls. Also, if the stent 22 is placed where there is a branching or other joining artery, blood can flow between the loops of the coil into the branch.

The stents and methods of the present invention provide improvements in the simplicity of the apparatus and its ease of use. Another advantage of the coiled shapes is that they are flexible, and can easily traverse bends and curves in the vasculature during insertion. When it is time to remove the stents, they are deformed to a configuration that can be easily removed from the vasculature by heating the stent and pulling on the connecting member.

It should be appreciated that the products and methods of the present invention are capable of being incorporated in the form of a variety of embodiments, only a few of which have been illustrated and described above. The invention may be embodied in other forms without departing from its spirit or essential characteristics. For example, the elongated member used to make the coil stent may have solid cross sections of a variety of shapes. The polymers used to form the stent may be surface-modified with drugs, or porous members may be loaded with drugs. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A method for intravascular delivery of a medication or a drug to a vascular site in the vascular system of a patient said vascular site being a coronary artery, said method comprising the steps of:

providing a medication or drug;

providing a catheter, said catheter comprising: an elongate shaft with a proximal end and a distal end, the proximal end being substantially linear, the distal end comprising a circumferentially continuous elongate member having two configurations, an elongated configuration, and an expanded configuration wherein said distal end is coiled about an axis that is substantially parallel to the proximal end, the coiled distal end having a length L greater than its outer diameter D, the shaft also having a drug delivery lumen extending from the proximal end to the distal end, the distal end of the shaft having a plurality of holes in fluid communication with the drug delivery lumen;

introducing the catheter into the vascular system of a patient, the catheter to the vascular site, the catheter having an outer diameter D of about 0.04–0.16 inches and an inner diameter d of about 0.03–0.13 inches while in said vascular site, and wherein when the distal end is in its expanded configuration, said holes at the distal end of the drug delivery lumen face an internal wall of the vascular site; and delivering the drug or medication through the drug delivery lumen and the holes at the distal end of the drug delivery lumen to the coronary artery.

2. A method for delivering and infusing drugs to a vascular site in the vascular system of a patient, said vascular site being a coronary artery, said method comprising:

providing a drug to be administered;

providing a catheter, said catheter having an elongated tubular body comprising a proximal end, a distal end, a proximal segment, and a distal infusion segment, said catheter having an infusion lumen formed therein extending along the axis of the elongated tubular body from the proximal end to the distal infusion segment, and a plurality of infusion ports formed in and distributed along the length and around the circumference of the distal infusion segment, said distal infusion segment of the catheter having a first, expanded helical coil infusion configuration and a second, elongated configuration;

introducing the catheter into the vascular system of a patient;

advancing the catheter to a desired infusion site at a coronary artery, allowing said distal infusion segment of the catheter to assume its first, expanded helical coil infusion configuration of at least two turns extending axially and outwardly from the proximal segment, when positioned at the desired infusion site;

delivering the drug through the infusion ports to the coronary artery.

3. The method of claim 2 wherein said infusion ports face an internal wall of the vascular site when the distal infusion segment is in its expanded helical coil configuration.

4. The method of claim 2 wherein the second elongated configuration of the distal infusion segment is a removal configuration, the method further comprising the step of causing the distal infusion segment to assume its removal configuration and removing the catheter, following delivery of the drug to the vascular site.

5. The method of claim 2 wherein first expanded helical coil configuration of the distal infusion segment has at least three turns extending axially and outwardly from the proximal segment.

* * * * *

UNITED STATES PATENT AND TRADEMARK OFFICE
CERTIFICATE OF CORRECTION

PATENT NO. : 5,795,318

DATED : August 18, 1998

INVENTOR(S) : Lixiao Wang et al.

It is certified that error appears in the above-identified patent and that said Letters Patent is hereby corrected as shown below:

Col. 1, line 37, after "less" insert -- traumatic alternative to bypass surgery. Two of these --;

Col. 8, line 31, after "flat side" insert -- side, with the holes 64 or 84 placed in only that flat side, which --;

Signed and Sealed this

Sixteenth Day of February, 1999

Attest:

Attesting Officer

Acting Commissioner of Patents and Trademarks